United States Patent [19]
Gilchrist

[11] Patent Number: 5,084,186
[45] Date of Patent: Jan. 28, 1992

[54] SEDIMENTATION CONTROL PROCESS

[76] Inventor: Ian C. R. Gilchrist, 13 De Waru Avenue, Selwyn, Roodepoort, Transvaal, South Africa

[21] Appl. No.: 539,823

[22] Filed: Jun. 19, 1990

[30] Foreign Application Priority Data

Jun. 20, 1989 [ZA] South Africa .................. 89/4673

[51] Int. Cl.$^5$ .................................................. C02F 1/56
[52] U.S. Cl. ..................................... 210/709; 210/725; 210/727; 210/734
[58] Field of Search ............... 210/702, 709, 725, 727, 210/726, 734, 96.1, 143

[56] References Cited

U.S. PATENT DOCUMENTS

| | | | |
|---|---|---|---|
| 4,388,195 | 6/1983 | von Hagel et al. | 210/725 |
| 4,544,489 | 10/1985 | Campbell et al. | 210/709 |
| 4,654,139 | 3/1987 | Baba et al. | 210/96.1 |
| 4,855,061 | 8/1989 | Martin | 210/709 |

Primary Examiner—Peter Hruskoci

[57] ABSTRACT

Sedimentation in an inherently colloidally stable mixture comprising a suspension of solids in a liquid is controlled by a five-step process. In the first step a mathematical model representing a relationship between certain parameters, namely area product, viscosity and a parameter related to zeta-potential, is created. In the second step, zones in the model in which there is undesirably high viscosity are identified, In the thrid step, a model sedimentation path which skirts the high viscosity zones is superimposed on the model. In the fourth step, the actual mixture under consideration is monitored during a sedimentation process to obtain actual measured values of any or all of the critical parameters. In the final step, the parameters are adjusted as necessary to fit actual measured values to values on the model sedimentation path.

11 Claims, 2 Drawing Sheets

SEDIMENTATION CONTROL PROCESS

BACKGROUND TO THE INVENTION

This invention relates to the control of viscosity. In one application, the invention is concerned with controlling the viscosity of clay suspensions created by mineral processing operations.

In the mineral processing industry, problems are encountered if the viscosity of slimes, which are to be disposed of in a slimes dam or other disposal facility, is too high. Amongst such problems are those of low pumpability and high wear of mechanical equipment.

A clay particle, when introduced to an aqueous medium, may assume a surface charge due to interaction with this medium. The magnitude of this charge is dependant on the surface chemistry of the solid and the composition of the medium. Where the concentration of charged particles in the medium is high, adjacent particles may be sufficiently close to one another allow the predomination of electrostatic interactions which are greater in magnitude than the gravitational force exerted on individual particles.

This results in a colloidally-stable suspension in which, by definition, the contained particles can not migrate downwardly under gravity.

In order to effect solid/liquid separation by gravitational means, a common approach is to reduce the surface charge on the particles either by modifying the ionic composition of the medium or by chemical reaction between an introduced species and the particle.

The charge on the particle surface can be approximated by measurement of a bulk property known as zeta-potential. The zeta-potential is defined as the electrical potential which exists between the particle surface and the layer of counter-ions which surround it in the aqueous medium. Particles having a zeta-potential of $-15\text{ mV}<\xi<15\text{ mV}$ are observed to settle naturally in aqueous media. Under these conditions, London—Van der Waal's forces predominate over the repulsive forces and mutual attraction takes place between adjacent particles. Discrete agglomerates of coagulated particles, termed "flocs", are thereafter able to settle at a greater velocity due to their increased effective mass.

The particle orientation contained within colloidal clay suspensions is the result of the electrochemical and electrostatic interactions between the particle surface and the medium. The bulk rheology is therefore indicative of this orientation and it is implicit that the rheology may be altered by modifying the composition of the medium.

Where the concentration of particles in suspension is sufficiently high, reduction of their zeta-potential can lead to spontaneous gelation through mutual interaction of the particles. In some suspensions, zeta-potential can be reduced by increasing the pH of the mixture and in others by adding an inorganic salt.

Gelation is undesirable in mineral processing applications since the resultant highly viscous gel may be extremely difficult to dispose of using conventional slimes disposal techniques.

The present invention seeks to provide a process for treating a colloidally-stable solid/liquid mixture so that undesirably high viscosity levels are avoided.

SUMMARY OF THE INVENTION

The invention provides a process for controlling sedimentation in an inherently colloidally-stable mixture comprising a suspension of solids in liquid, the process including:
 a) creating a mathematical model (or process model) representing, for the same or a similar mixture, a relationship between at least three parameters of the mixture, such parameters including firstly area product of the mixture, secondly viscosity of the mixture and thirdly a parameter related to the zeta-potential of particles in the mixture;
 b) identifying in the model zones where viscosity of the mixture is undesirably high;
 c) superimposing on the model a model sedimentation path which avoids the zones of undesirably high viscosity;
 d) monitoring the actual mixture to obtain actual measured values of any or all of the parameters during a sedimentation process; and
 e) adjusting any or all of the parameters as necessary to fit the actual measured values to values on the model sedimentation path.

The parameter "area product" is representative of the total surface area of the particles per unit of volume of mixture and may be calculated as the product of specific surface area of the particles and suspended solids content. The value "suspended solids content" is calculated as the mass of suspended solids per unit volume of the suspension, while the value "specific surface area" is calculated on the basis of knowledge of the shape and size distribution of solids in the suspension, as the total surface area of a unit mass of the particles.

In a preferred form of the invention, step c) involves superimposing on the mathematical model a model sedimentation path of which certain sections represent equal turbidity of the mixture for varying first, second and third parameters, and of which other sections represent constant area product of the mixture for varying second and third parameters.

The third parameter may be pH of the mixture or concentration in the mixture of an appropriate inorganic salt adapted to reduce zeta-potential. In the former case, step d) may comprise the steps of controlling the area product by dilution with a suitable diluent such as clear water, increasing the pH of the mixture by adding an appropriate coagulating alkali such as lime, adding a flocculating agent to the mixture to cause flocculation of the mixture and sedimentation of solid flocs, and repeating any or all of these steps as necessary to fit the actual measured values obtained in step d) to values on the model sedimentation path. In the latter case, the step of increasing the pH may be replaced by the step of increasing the concentration of the inorganic salt, the other steps remaining the same.

BRIEF DESCRIPTION OF THE DRAWINGS

The invention will now be described in more detail, by way of example only, with reference to the accompanying drawings in which.

SPECIFIC DESCRIPTION

Figure 2:
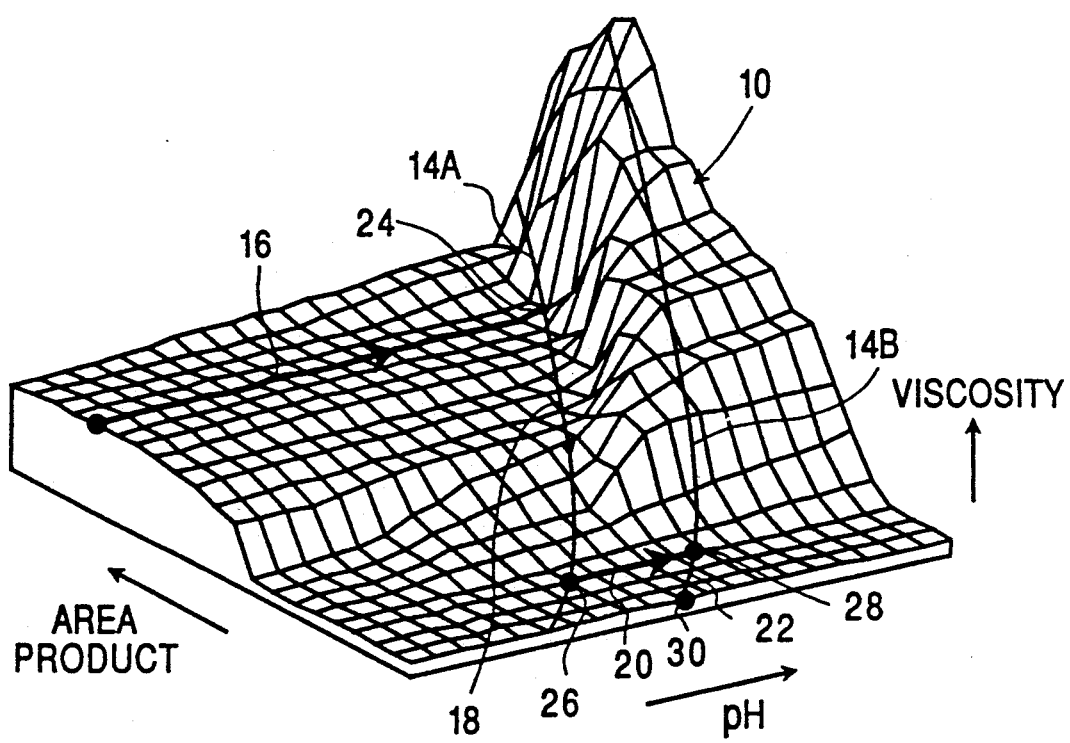
FIG. 2 shows a three-dimensional graphical representation of a mathematical model in accordance with which the process of the invention operates.
Figure 3:
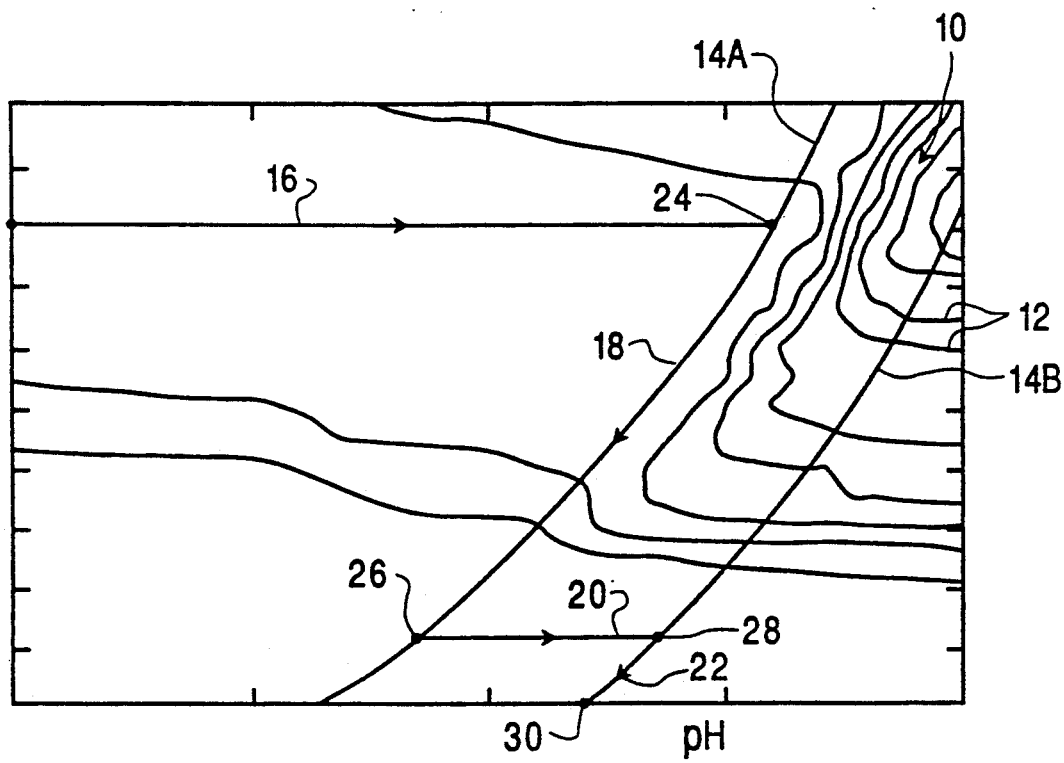
FIG. 3 shows the graphical representation of FIG. 2 in two dimensions and is effectively a plan view of the graphical representation of FIG. 2.

Reference is made firstly to FIGS. 2 and 3 which graphically represent a mathematical model of a clarification regime for a typical inherently colloidally-stable mixture comprising a suspension of clay particles in water. A mixture of the kind under consideration may typically be produced as waste from a mineral processing operation. As indicated previously, it is desirable to clarify the mixture at least to a degree compatible with efficient disposal in a slimes dam or other disposal zone.

FIG. 2 shows a three-dimensional graphical representation of a mathematical model created from prior knowledge obtained about the kind of mixture which is to be encountered. In this representation, the three axes represent values of three different parameters, being viscosity on the vertical axis, pH on one horizontal axis and area product, as discussed above, on the other horizontal axis. The three-dimensional representation shows a peak zone 10 which is a zone in the sedimentation regime of unacceptably high viscosity. FIG. 3 shows what is effectively a plan view of the graphical representation seen in FIG. 2, values of viscosity being indicated by means of "contour lines" 12 joining points of equal viscosity. Also plotted on FIGS. 2 and 3 are lines 14 of equal turbidity of the mixture, i.e. lines joining all points of equal turbidity. Turbidity may, for instance, be measured in nephelometric turbidity units (NTU), the line 14A linking points at, say, 5000 NTU and the line 14B linking points at, say, 40 NTU.

Once the mathematical model has been created, it is necessary for the process designer to superimpose thereon a model or desired sedimentation path. In FIGS. 2 and 3, this path is indicated by the numerals 16, 18, 20 and 22, with set points 24, 26, 28 and 30 on the path.

It will be observed that the model sedimentation path avoids the high viscosity zone 10. The object of the apparatus described below is to fit an actual sedimentation path to the model path, and thereby to prevent unacceptably high viscosities in the mixture.

Figure 1:
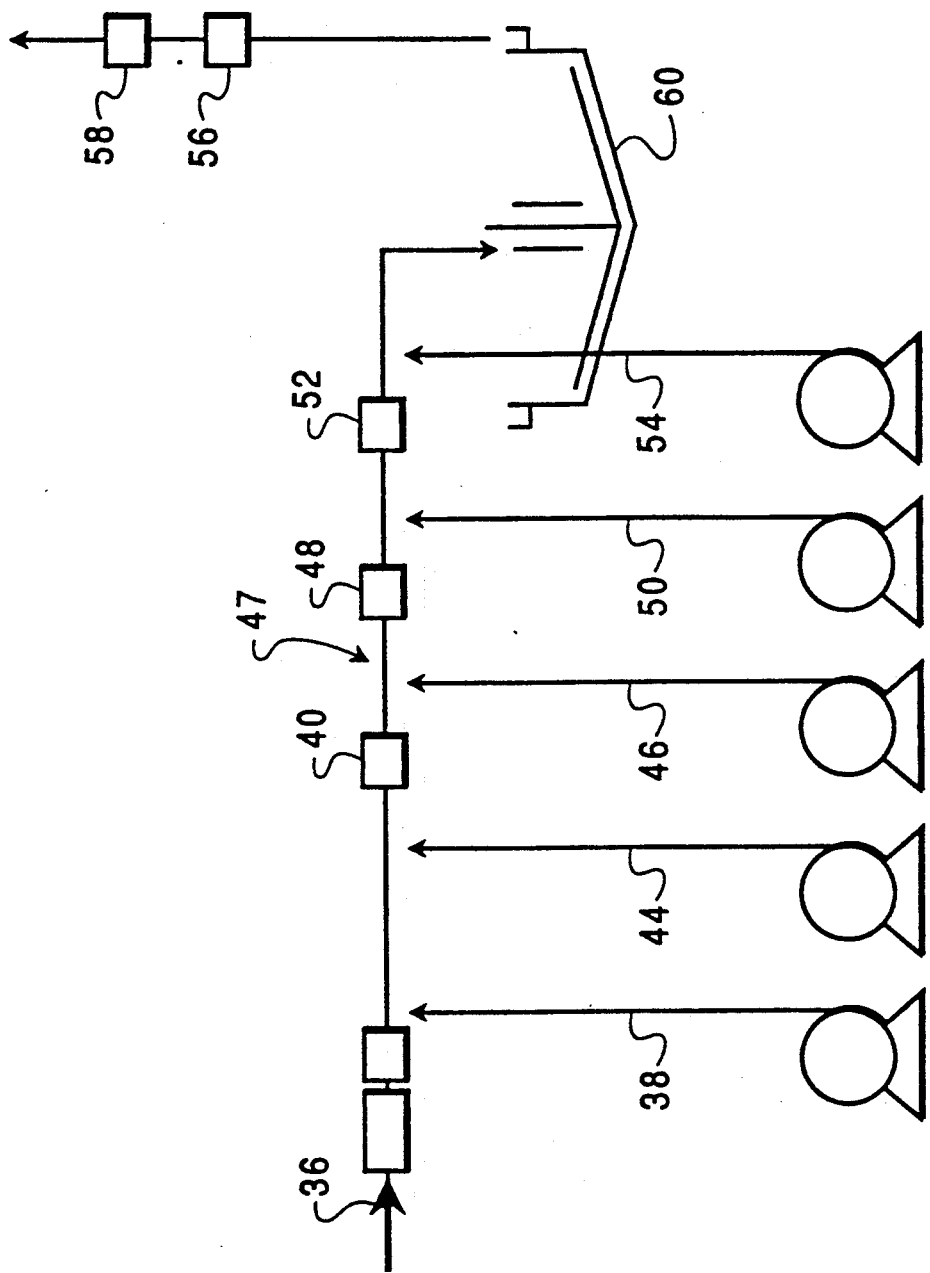
FIG. 1 shows a schematic view of apparatus used in the process of the invention.

FIG. 1 shows the apparatus which is used to fit the actual path to the model path. The stream 36 of mixture is diluted with a diluent, in this case clear water, entering the stream via a dilution line 38 controlled by a feedback controller (not shown) to keep the area product of the mixture at a value corresponding to that of the first set point 24 in FIGS. 2 and 3. The pH of the stream 36 is measured by a pH meter 40. Signals produced by the meter 40 are processed by a pH controller (not shown) which controls the addition of calcium hydroxide through a line 44. The addition of the lime creates a concentration of calcium monohydroxyl species, decreases the zeta potential of the particles in the mixture and increases the pH. Thus the pH in this example relates to the zeta potential in that an increase in pH decreases the zeta potential. The pH controller ensures that the rate of lime addition is such as to maintain the actual pH at the level of the set point 24. It will be appreciated that over-addition of lime at this stage would lead the actual sedimentation path into the peak zone 10.

Flocculant is added to the feed stream 36 via a flocculant line 46. The addition of flocculant results in partial removal of suspended solids in the mixture. Although the flocculated solids then remain in the mixture, they no longer contribute to the colloidally stable fraction of the mixture. The solids content of the colloidally stable fraction is measured by a turbidity meter 48 which produces signals that are processed by the feedback controller mentioned above which in turn controls the addition of clear water through the line 38 so as to maintain the original area product level at a value corresponding to that of the set point 24.

The above sequence of operations is represented in FIGS. 2 and 3 by the section 16 of the model sedimentation path.

As the partially flocculated mixture continues downstream in the process, its overall solids content remains constant but the pH of the mixture tends to decrease as a result of dilution by the flocculant. In addition, the turbidity of the stream remains constant. This part of the operation is represented in FIGS. 2 and 3 by movement along the section 18 of the model sedimentation path. As illustrated, this section follows the line 14A of equal turbidity to bring the process stream to the condition represented by the set point 26 in FIGS. 2 and 3.

Thus it will be seen that the path from points 24 to 26 in FIG. 3, corresponding in FIG. 1 to the stage between the addition point 47 and the meter 48, corresponds to a reduction in pH and area product while overall solids content has remained constant. At the same time, the viscosity has dropped slightly by virtue of floc sedimentation of solids from the colloidally stable or rheologically active fraction of the mixture. Between the points 24 and 26, the mixture does not enter the zone 10 of unacceptably high viscosity so spontaneous gelation is avoided.

Further downstream, more lime is added via a line 50. This addition has the same general effect as the previous addition of lime, namely to decrease the zeta-potential still further and increase the pH still further. This part of the operation is represented in FIGS. 2 and 3 by the section 20 of the model path to bring the actual process condition to the set point 28. A pH control is carried out using a pH meter 52 and associated pH controller which in turn controls the introduction of lime through the line 50.

Further downstream, more flocculant is added via a line 54 which causes the actual process condition to change along the section 22 of the model path i.e. along the line 14B of equal turbidity. A further turbidity meter 56 performs a function similar to that of the turbidity meter 48.

A final pH meter 58 monitors the pH of the stream at the end of the process and, with the assistance of an appropriate controller, ensures the the final process condition is that represented by the set point 30 in FIGS. 2 and 3. A sedimentation tank 60 is provided to capture sedimentary flocs produced in the process. The final part of the operation is represented by the section 22 of the model path, bringing the process stream which results at the end of the process to the set point 30. The section 22 represents changes along the equal turbidity line 14B in FIGS. 2 and 3 and corresponds to the earlier section 18 on the model path.

In this embodiment, the steps of lime addition with pH control and flocculant addition with control of turbidity are carried out only twice to arrive at the point 30 which is considered to represent an acceptable effluent. However, depending on the specific circumstances in practice, these steps may be carried out many more times to bring the turbidity of the final stream to the desired level while skirting the zone(s) of unacceptably high viscosity.

It will be appreciated that in this embodiment the pH parameter is related to the zeta potential of the solid particles. In other processes it may be preferable to adjust the zeta potential by addition of an appropriate inorganic salt. In such cases, the mathematical model will be created with the pH parameter replaced by concentration of the salt. Thus in the graphical representation of the mathematical model the pH axis would be replaced by a salt concentration axis. In the apparatus itself, the pH meters would be replaced by salt concentration meters.

The flocculant which is used may be a polyacrylamide flocculant.

I claim:

1. A process for preventing gel formation during sedimentation in an inherently colloidally-stable mixture comprising a suspension of solids in liquid, the process comprising the steps of:
   a) deriving a process model for the mixture representing a relationship between at least three parameters of the mixture, said at least three parameters including: a first parameter related to an area product of the mixture being representative of the total surface area of the particles per unit of volume of mixture, a second parameter representing a viscosity of the mixture, and a third parameter related to zeta-potential of solid particles in the mixture;
   b) identifying zones in the process model wherein the second parameter represents a viscosity such that spontaneous gelation is likely to take place;
   c) superimposing on the process model a model sedimentation path which avoids the zones where spontaneous gelation is likely to take place;
   d) monitoring the mixture to obtain actual values for the parameters during a sedimentation process; and
   e) adjusting the parameters of said mixture as necessary to fit the actual values to values on the model sedimentation path so that spontaneous gelation is avoided in said mixture during said sedimentation process.

2. A process according to claim 1 wherein step c) of the process comprises superimposing on the process model a model sedimentation path of which certain sections represent equal turbidity of the mixture for varying values of the first, second and third parameters, and of which other sections represent constant area product of the mixture for varying values of the second and third parameters.

3. A process according to claim 1 wherein the third parameter is pH of the mixture.

4. A process according to claim 3 wherein step d) of the process comprises the steps of controlling the area product of the mixture by dilution with a diluent, increasing the pH of the mixture by adding an appropriate coagulating alkali, adding a flocculating agent to the mixture to cause flocculation of the mixture and sedimentation of solid flocs, and repeating any or all of these steps as necessary to fit the actual values obtained in step d) to values on the model sedimentation path.

5. A process according to claim 4 wherein the alkali is lime.

6. A process according to claim 4 wherein the diluent is clear water.

7. A process according to claim 4 wherein the flocculating agent is a polyacrylamide flocculant.

8. A process according to claim 1 wherein the third parameter is concentration in the mixture of an appropriate inorganic salt adapted to reduce zeta-potential.

9. A process according to claim 8 wherein step d) of the process comprises the steps of controlling the area product of the mixture by dilution with a diluent, reducing the zeta-potential of the mixture by adding the inorganic salt, adding a flocculating agent to the mixture to cause flocculation of the mixture and sedimentation of solid flocs, and repeating any or all of these steps as necessary to fit the actual values obtained in step d) to values on the model sedimentation path.

10. A process according to claim 9 wherein the diluent is clear water.

11. A process according to claim 9 wherein the flocculating agent is a polyacrylamide flocculant.

* * * * *